United States Patent [19]

Dürr

[11] 4,389,236
[45] Jun. 21, 1983

[54] HERBICIDAL 3-PHENOXYMETHYLENE-ANILINES

[75] Inventor: Dieter Dürr, Bottmingen, Switzerland

[73] Assignee: Ciba-Geigy Corporation, Ardsley, N.Y.

[21] Appl. No.: 289,582

[22] Filed: Aug. 3, 1981

[30] Foreign Application Priority Data

Aug. 15, 1980 [CH] Switzerland ............ 6198/80

[51] Int. Cl.³ ............ A01N 43/84; A01N 43/40; A01N 37/52; C07C 123/00; C07C 119/18; C07D 295/18

[52] U.S. Cl. .................. 71/88; 71/92; 71/94; 71/95; 71/121; 260/453.7; 564/246; 542/414; 542/423; 544/167; 544/398; 546/232; 548/300; 548/341; 548/352; 548/356; 548/379; 548/561; 548/565; 548/566

[58] Field of Search ............ 564/246; 260/453.7, 260/326.5 L, 326.85; 71/121, 88, 92, 94, 95; 542/414, 423, 424, 425; 548/300, 341, 352, 356, 379, 561, 565, 566; 544/167, 398; 546/232

[56] References Cited

U.S. PATENT DOCUMENTS 3,715,436 2/1973 Janiak et al. ............ 260/453.7
3,781,357 12/1973 Duerr et al. ............ 71/121

FOREIGN PATENT DOCUMENTS 1353726 1/1964 France .
1504840 10/1967 France .

OTHER PUBLICATIONS

C.A. 79:28397q (1973), Japanese Kokai 70-01123.
C.A. 80:44678h (1974), Japanese Kokai 72-49691.

Primary Examiner—Natalie Trousof
Assistant Examiner—L. Hendriksen
Attorney, Agent, or Firm—Frederick H. Rabin

[57] ABSTRACT

The invention relates to 3-phenoxymethylene-anilines of the formula

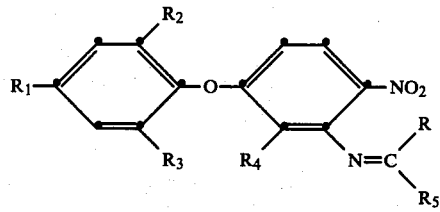

wherein
R is a

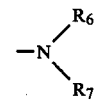

radical or $C_1$–$C_4$ alkoxy,
R is halogen or $C_1$–$C_2$ haloalkyl,
$R_2$, $R_3$ and $R_4$, each independently of the other, are hydrogen or halogen
$R_5$ is hydrogen or $C_1$–$C_4$ alkyl
$R_6$ is hydrogen, $C_1$–$C_4$ alkyl, $C_2$–$C_4$ alkenyl or $C_2$–$C_4$ alkynyl, and
$R_7$ is hydrogen or $C_1$–$C_4$ alkyl, while $R_5$ and $R_6$, or $R_6$ and $R_7$, together with the nitrogen atom to which they are attached, can form a heterocyclic ring system which may be interrupted by further hetero-atoms.

Where R is a —$NR_6R_7$ radical, the salts with acids also fall within the scope of formula I. These compounds have excellent selective herbicidal properties.

14 Claims, No Drawings

HERBICIDAL 3-PHENOXYMETHYLENE-ANILINES

The present invention relates to novel herbicidally active 3-phenoxymethylene-anilines, to the production thereof, to herbicidal compositions containing them, and to the use thereof for controlling weeds, in particular selectively, in crops of useful plants.

The 3-phenoxymethylene-anilines of this invention have the general formula I

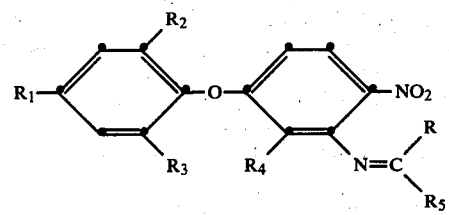

wherein
R is a

radical or $C_1$–$C_4$alkoxy,
$R_1$ is halogen or $C_1$–$C_2$haloalkyl,
$R_2$, $R_3$ and $R_4$, each independently of the other, are hydrogen or halogen,
$R_5$ is hydrogen or $C_1$–$C_4$alkyl,
$R_6$ is hydrogen, $C_1$–$C_4$alkyl, $C_2$–$C_4$alkenyl or $C_2$–$C_4$alkynyl, and
$R_7$ is hydrogen or $C_1$–$C_4$alkyl, whilst $R_5$ and $R_6$, or $R_6$ and $R_7$, together with the nitrogen atom to which they are attached, can form a heterocyclic ring system which may be interrupted by further hetero-atoms.

The salts which the amidines are able to form with acids (R in formula I is then —$NR_6R_7$) also fall within the scope of formula I.

Various formamidines having microbicidal, ectoparasiticidal, insecticidal or fungicidal properties are described in Japanese patent publications J 4 801 123 and J 7 249 691 and in French patent specifications 1 353 726 and 1 504 840.

Halogen in the definitions of $R_1$ to $R_4$ denotes fluorine, chlorine or bromine, preferably fluorine, with chlorine being most preferred.

Alkyl denotes straight-chain or branched alkyl, e.g. methyl, ethyl, n-propyl, isopropyl or the four butyl isomers. Straight-chain radicals are preferred.

Alkoxy radicals in the definition of R are straight-chain radicals such as methoxy, ethoxy, n-propyloxy and n-butyloxy.

By analogy, haloalkyl denotes in general fluoromethyl, chloromethyl, α-chloroethyl, β-chloroethyl, trifluoromethyl, or α,α,β,β-tetrachloroethyl, with chloromethyl and trifluoromethyl being preferred.

Alkenyl is e.g. vinyl, allyl, methallyl and crotyl, with vinyl and allyl being preferred.

Alkynyl is e.g. ethynyl and, preferably, propargyl.

Examples of possible nitrogen-containing heterocyclic rings are pyrrolidine, pyrroline, imidazolidine, pyrazolidine, piperidine, piperazine, morpholine, pyrazoline, imidazole, pyrrole or imidazoline, with pyrrolidine, piperidine and morpholine being preferred.

Examples of acids which are able to form salts with the amidines are inorganic acids such as hydrochloric acid, hydrobromic acid, sulfuric acid and phosphoric acid; or organic acids, e.g. toluenesulfonic acid, or unsubstituted or halogenated mono- or dicarboxylic acids, e.g. formic acid, acetic acid, trichloroacetic acid, trifluoroacetic acid, oxalic acid and methanesulfonic acid or phthalic acid.

Preferred compounds on account of their action are the compounds of formula I, in which R is the amino group —$NR_6R_7$.

Further preferred compounds are the compounds of formula I, in which $R_1$ is the trifluoromethyl group.

Compounds of formula I, in which one to two of $R_2$, $R_3$ and $R_4$, each independently of the other, are chlorine atoms and the others are hydrogen, have a particularly good selective action.

Especially preferred compounds are the compounds of formula I, in which $R_1$ is trifluoromethyl, $R_2$ is chlorine and $R_3$ and $R_4$ are hydrogen, or in which one of $R_3$ and $R_4$ is chlorine and the other is hydrogen.

The 3-phenoxymethylene-anilines of the formula I are obtained by methods which are known per se.

In a first process, the compounds of the subformula Ia

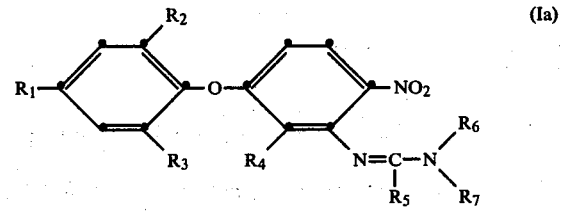

are obtained by reacting a nitroaniline of the formula II

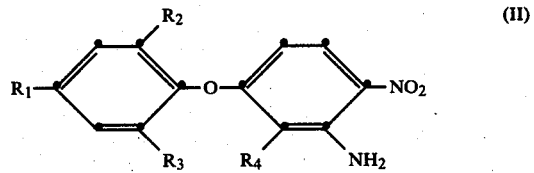

in the presence of a condensation agent and optionally of a base, with a carbamide of the formula III

and, if desired, converted into their salts. In the formulae Ia, II and III above, $R_1$ to $R_7$ are as defined for formula I.

Examples of suitable condensation agents are thionyl chloride, phosgene, phosphoroxy trichloride, phosphorus pentachloride, phosphorus trichloride, dimethyl sulfate or p-toluenesulfonyl chloride. Examples of suitable bases are sodium hydroxide and potassium hydroxide, sodium bicarbonate, sodium carbonate, calcium oxide or calcium carbonate.

In another process, the compounds of the subformula Ia are obtained by reacting an aniline of the formula II with a carbamide diacetal of the formula IV

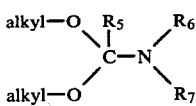

wherein $R_5$ to $R_7$ are as defined for formula I and alkyl is straight-chain $C_1$-$C_4$alkyl, and, if desired, converted into their salts.

Finally, in a further process it is possible to obtain the compounds of the subformula Ib

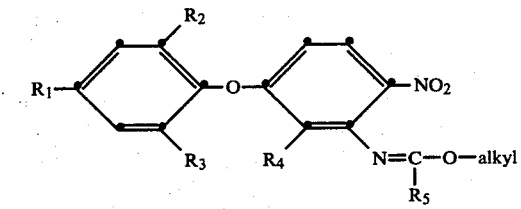

by reacting an aniline of the formula II with an orthoester of the formula V

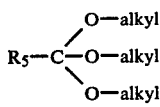

wherein alkyl and $R_1$ and $R_5$ are as defined for formula IV.

The compounds of the formula Ia can also be obtained by reacting an iminoether of the formula Ib with an amine of the formula VI

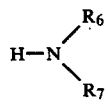

wherein $R_6$ and $R_7$ are as defined for formula I.

The salts of the amidines Ia are obtained by dissolving the amidines in an inert solvent, reacting them with equimolar amounts of acid, and removing the solvent by evaporation.

These reactions are conveniently conducted in inert organic solvents such as methanol, ethanol, isopropanol, methylene chloride, chloroform, tetrahydrofurane, dioxane, acetonitrile or toluene.

The compounds of the formula I are stable compounds and no precautionary measures are required for handling them.

The compounds of the formula I are novel and have an interesting herbicidal and plant growth regulating action In particular, they have excellent selective herbicidal properties which make them most suitable for use in crops of cultivated plants such as rice, maize, millet, cereals, cotton soybeans, sugar beet, vegetables of all kinds and ornamentals, but preferably in wheat.

Compared with that of known compounds, the herbicidal action of the compounds of the formula I takes effect even at very low rates of application. In general, the rates of application are from 0.005 to 5 kg, with the preferred range being from 0.25 to 2 kg per hectare.

The compounds of the formula I can be used for controlling weeds preemergence or postemergence. Preferably, however, the compounds or compositions containing them are applied postemergence.

Furthermore, the compounds of formula I regulate plant growth. The manner in which they influence plant growth differs. Accordingly, they inhibit, delay or suppress in particular growth and germination. The compounds thus have both a pre- and postemergence herbicidal action and a growth inhibiting action.

Compositions which contain at least one compound of the formula I as active component are particularly suitable for inhibiting and controlling the growth of monocots and dicots such as grasses, shrubs, trees, crops of cereals and leguminosae, sugar cane, tobacco, soybeans, onion and potato tubers, ornamentals, fruit trees and vines.

The primary effect attained by the compounds of the formula I consists in the desired reduction of the plant size, in particular of the growth in height. In general, a certain change in the form of the plant is allied to this reduction in size. As a direct consequence of the reduction of the growth in height the plant is strengthened: leaves and stems are better developed. By shortening the distances between internodes in monocots the breaking strength is increased. It is thus possible substantially to prevent harvest losses caused by thunderstorms, prolonged rainfall etc., which usually result in a lodging of crops of cereals and leguminous plants, and thereby to facilitate harvesting. As side-effect, the reduced growth in height of useful plants results in a saving of fertilisers. This also applies equally to ornamentals and ornamental grass plots, turf for sporting activities or other grass-covered open spaces.

One of the greatest problems posed by pure grass cultivations, however, is the actual cutting of the grass itself, whether in open spaces of urban areas, industrial sites, playing fields, along main roads, on airport runways, on railway embankments or the embankments of water bodies. In all these cases it is necessary to cut the turf or grass periodically. This operation is not only time-consuming, complicated and expensive in respect of labour and machinery, but involves the personnel concerned and traffic users in considerable hazard.

For this reason there is an urgent need in areas with extensive traffic networks on the one hand to maintain and tend the grassy covering for strengthening road shoulders and embankments on traffic routes, and on the other to keep it at a reasonable height by simple means during the entire vegetation period. This need is fulfilled in a very avantageous manner by applying the compounds of the formula I.

In certain crops the compounds of formula I are able to desiccate the leaves shortly before fruit ripening and to cause them to drop. This action is advantageous whenever the crop in question is to be harvested mechanically. The compounds of the present invention are therefore also suitable for use as defoliants and desiccants in cotton and potatoes shortly before harvesting.

In addition to their herbicidal properties, a number of the compounds of formula I also have insecticidal, acaricidal, ovicidal, ectoparsiticidal, nematicidal and fungicidal properties.

The invention also relates to herbicidal compositions which contain a novel compound of the formula I, as well as to methods of controlling monocot and dicot weeds pre- and postemergence, preferably dicot weeds, in crops of useful plants such as maize, rice, millet and cereals, especially in wheat crops.

The compositions of the present invention are obtained in known manner by intimately mixing and grinding active ingredients (compounds) of the formula I with suitable carriers and/or adjuvants, if desired or necessary with the addition of antifoams, wetting agents, dispersants and/or solvents which are inert to the active ingredients. The active ingredients can be processed to the following formulations:

solid formulations:
   dusts, tracking powders, granules (coated granules, impregnated granules and homogenous granules), concentrates which are dispersible in water:
   wettable powders, pastes, emulsions, emulsifiable concentrates, suspension concentrates (flowables);
liquid formulations:
   solutions.

The concentrations of active ingredient in the compositions of this invention are from 0.1 to 95% by weight, preferably from 1 to 80% by weight. Formulations can also be diluted to concentrations as low as 0.001% by weight.

The compositions of the present invention can be mixed with other biocidal compounds or compositions. Thus in addition to containing the compounds of the formula I, the compositions of the invention can also contain e.g. insecticides, fungicides, bactericides, fungistats, bacteriostats, nematocides or further herbicides, in order to broaden the activity spectrum.

The invention is illustrated by the following Examples in which parts and percentages are by weight and pressures are in millibars, (mb) (mb=100 pascal).

EXAMPLE 1

N-[3-(2'-Chloro-4'-trifluoromethylphenoxy)-6-nitrophenyl]-N',N'-dimethylformamidine

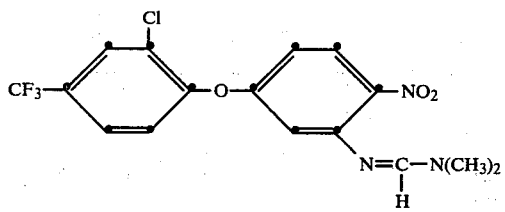

(a) 25.2 g of 2-chloro-4-trifluoromethyl-3',4'-dinitrodiphenyl ether in a mixture of 240 ml of acetonitrile and 9 g of 30% ammonia solution are heated for 1 hour to 150° C. in an autoclave. The solution is then concentrated. Recrystallisation of the residue yields 21 g of 3-(2'-chloro-4'-trifluoromethylphenoxy)-6-nitroaniline with a melting point of 86°–92° C.

(b) 16.5 g of 3-(2'-chloro-4'-trifluoromethylphenoxy)-6-nitroaniline and 8 g of dimethyl formamide diethyl acetal are refluxed in 50 ml of absolute alcohol for 16 hours and the solution is then concentrated. The residue is distilled in a bulb tube at 230° C./0.09 mb, affording 18 g of N-[3-2'-chloro-4'-trifluoromethylphenoxy)-6-nitrophenyl]-N',N'-dimethylformamidine as a viscous yellow oil (compound 1).

Compound 1 and compounds prepared in analogous manner are listed in the following table.

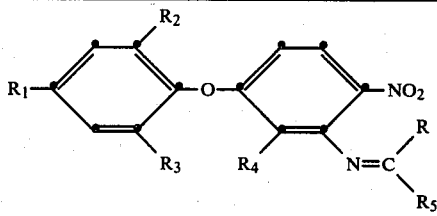

| No. | R | $R_1$ | $R_2$ | $R_3$ | $R_4$ | $R_5$ | Physical data (°C.) |
|---|---|---|---|---|---|---|---|
| 1 | —N(CH$_3$)$_2$ | CF$_3$ | Cl | H | H | H | b.p. 230°/0.09 mb. |
| 2 | —N(CH$_3$)$_2$ | CF$_3$ | Cl | H | H | CH$_3$ | b.p. 225°/0.03 mb. |
| 3 | —N⟨morpholino⟩ | CF$_3$ | Cl | H | H | H | |
| 4 | —N(CH$_3$)C$_4$H$_9$ | CF$_3$ | Cl | Cl | H | H | |
| 5 | —N⟨piperidino⟩ | CF$_3$ | Cl | Cl | H | H | |
| 6 | —NHCH$_3$ | CF$_3$ | Cl | H | Cl | H | |
| 7 | —N(C$_4$H$_9$)$_2$ | CF$_3$ | Cl | H | Cl | H | |
| 8 | —OC$_2$H$_5$ | Cl | Cl | H | Cl | H | |
| 9 | —OCH$_3$ | CF$_3$ | H | H | Cl | H | |
| 10 | —OC$_2$H$_5$ | CF$_3$ | H | H | Cl | CH$_3$ | |
| 11 | —N(CH$_3$)$_2$ | CF$_3$ | Cl | H | Cl | CH$_3$ | |
| 12 | —N⟨morpholino⟩ | CF$_3$ | Cl | H | Cl | H | |
| 13 | —NHCH$_3$ | CF$_3$ | Cl | H | H | H | |
| 14 | —OC$_2$H$_5$ | CF$_3$ | Cl | H | H | H | b.p. 220°/0.03 mb. |
| 15 | —OC$_2$H$_5$ | CF$_3$ | Cl | H | H | CH$_3$ | |
| 16 | —N⟨piperidino⟩ | CF$_3$ | H | H | Cl | H | |
| 17 | —N(CH$_3$)$_2$ | CF$_3$ | H | H | Cl | CH$_3$ | m.p. 110–113° |
| 18 | —N(CH$_3$)$_2$ | CF$_3$ | | | | H | m.p. 108–110° |
| 19 | —OC$_2$H$_5$ | CF$_3$ | Cl | H | Cl | CH$_3$ | |
| 20 | —N(CH$_3$)$_2$ | Cl | Cl | H | Cl | H | b.p. 250°/0.2 mb. |

EXAMPLE 2

Formulation of a dust

The following substances are used to formulate (a) a 5% and (b) a 2% dust:

(a)
   5 parts of N-[3-(2'-chloro-4'-trifluoromethylphenoxy)-6-nitrophenyl]-N',N'-dimethylformamidine,
   95 parts of talc;

(b)
   2 parts of the above compound,
   1 part of highly dispersed silicic acid
   97 parts of talc.

The active ingredient is mixed with the carriers and ground. Instead of compound 1, one of compounds 2–20 can be used with similar success.

EXAMPLE 3

Formulation of a paste

The following substances are used to formulate a 45% paste:
- 45 parts of N-[3-(2'-chloro-4'-trifluoromethylphenoxy)-6-nitrophenyl]-N',N'-dimethylformamidine or a salt thereof,
- 5 parts of sodium aluminium silicate,
- 14 parts of cetyl polyethylene glycol ether with 8 moles of ethylene oxide,
- 1 part of oleyl polyethylene glycol ether with 5 moles of ethylene oxide,
- 2 parts of spindle oil,
- 10 parts of polyethylene glycol (average mol. wt. 400 g/mole),
- 23 parts of water.

The active ingredient is homogeneously mixed with the adjuvants in appropriate devices and ground, to give a paste from which suspension of any desired concentration can be obtained by dilution with water.

EXAMPLE 4

Formulation of a wettable powder

The following constituents are used to formulate (a) a 50%, (b) a 25% and (c) a 10% wettable powder:

(a)
- 50 parts of compound 1 or a salt thereof,
- 5 parts of sodium dibutylnaphthylsulfonate,
- 3 parts of naphthalenesulfonic acid/phenolsulfonic acid/formaldehyde condensate (3:2:1),
- 22 parts of kaolin,
- 20 parts of chalk;

(b)
- 25 parts of compound 1
- 5 parts of sodium oleylmethyltauride,
- 2.5 parts of naphthalenesulfonic acid/formaldehyde condensate,
- 0.5 part of carboxymethyl cellulsoe,
- 5 parts of neutral potassium aluminium silicate,
- 62 parts of kaolin;

(c)
- 10 parts of a salt of compound 1,
- 3 parts of a mixture of the sodium salts of saturated fatty alcohols,
- 5 parts of naphthalenesulfonic acid/formaldehyde condensate,
- 32 parts of chalk,
- 50 parts of kaolin.

The active ingredient is applied to the corresponding carriers (kaolin and chalk) and then these are mixed and ground, to give wettable powders of excellent wettability and suspension power. By diluting these wettable powders with water it is possible to obtain suspensions of any desired concentration.

Instead of compound 1, one of compounds 2–20 can be used with similar success.

EXAMPLE 5

Formulation of a suspension concentrate

The following substances are used to formulate a 45% concentrate:
- 45 parts of a compound of formula I,
- 5 parts of ethylene glycol,
- 3 parts of octylphenoxypolyethylene glycol having 9–10 moles of ethylene oxide per mole of octylphenol,
- 3 parts of a mixture of aromatic sulfonic acids, condensed with formaldehyde as ammonium salt,
- 1 part of silicone oil in the form of a 75% emulsion,
- 0.1 part of a mixture of 1-(3-chloroallyl)-3,5,7-triazoazonium-adamantane chloride with sodium carbonate, chloride value at least 11.5%,
- 0.2 part of a bipolymeric thickener having a maximum of 100 nuclei per gram, and
- 42.7 parts of water.

The active ingredient is mixed with the adjuvants in appropriate devices and the mixture is ground. Suspensions of the desired concentration can be obtained by diluting the resultant paste with water.

BIOLOGICAL EXAMPLES

EXAMPLE 6

Preemergence herbicidal action (inhibition of germination)

In a greenhouse, plant seeds are sown in flower pots of 12–15 cm diameter. Immediately after sowing, the surface of the soil is treated with an aqueous dispersion or solution (obtained from an emulsifiable concentrate or wettable powder) of the compounds to be tested. Different concentrations of active ingredient per hectare are employed. The pots are then kept in the greenhouse at 22°–25° C. and 50–70% relative humidity. The test is evaluated 3 weeks later and the condition of the plants assessed in accordance with the following rating:
1 = plants totally withered
2–8 = intermediate stages of damage
9 = no action (as untreated controls)
— = plant not tested.

The results are reported in the following table.

| | Compound | | | | | | | | | | | | | | | |
|---|---|---|---|---|---|---|---|---|---|---|---|---|---|---|---|---|
| | 2 | | | | 14 | | | | 17 | | | | 18 | | | |
| | Rate of application in kg/hectare | | | | | | | | | | | | | | | |
| Plant | 4 | 2 | 1 | ½ | 4 | 2 | 1 | ½ | 4 | 2 | 1 | ½ | 4 | 2 | 1 | ½ |
| wheat | 2 | 4 | 7 | 7 | 7 | 8 | 9 | 9 | 2 | 6 | 8 | 9 | 9 | 9 | 9 | 9 |
| rice | 2 | 4 | 6 | 7 | 8 | 9 | 9 | 9 | 3 | 6 | 8 | 9 | 9 | 9 | 9 | 9 |
| soybeans | 4 | 6 | 9 | 9 | 9 | 9 | 9 | 9 | 8 | 9 | 9 | 9 | 9 | 9 | 9 | 9 |
| cotton | 5 | 6 | 7 | 7 | — | — | — | — | 6 | 7 | 9 | 9 | — | — | — | — |
| avena fatua | 2 | 2 | 2 | 6 | 1 | 2 | 4 | 9 | 2 | 2 | 4 | 8 | 2 | 6 | 7 | 9 |
| alopecurus myosuroides | 1 | 1 | 1 | 2 | 1 | 1 | 2 | 6 | 2 | 2 | 4 | 9 | 2 | 2 | 6 | 9 |
| echinochloa crus galli | 1 | 1 | 1 | 1 | 1 | 2 | 3 | 9 | 1 | 1 | 1 | 2 | 2 | 3 | 4 | 4 |
| rottboellia exaltata | 1 | 1 | 2 | 7 | 2 | 4 | 4 | 7 | 1 | 1 | 2 | 4 | 2 | 3 | 3 | 9 |
| abutilon | 1 | 1 | 1 | 1 | 1 | 1 | 8 | 9 | 1 | 1 | 1 | 3 | 1 | 1 | 1 | 1 |
| chenopodium album | 1 | 1 | 1 | 1 | 1 | 1 | 1 | 1 | 1 | 1 | 1 | 1 | 1 | 1 | 1 | 1 |
| viola tricolor | 1 | 1 | 1 | 1 | 1 | 1 | 1 | 1 | 1 | 1 | 1 | 1 | 1 | 1 | 1 | 1 |

EXAMPLE 7

Postemergence herbicidal action (contact action).

The plants, both monocot and dicot weeds and cultivated plants, are sprayed postemergence, in the 4- to 6-leaf stage, with an aqueous dispersion of the compound to be tested at different rates of concentration. The plants are then kept in the greenhouse at 24°–26° C. and 45–60% relative humidity. The test is complete after the treatment and the condition of the plants is assessed in accordance with the same rating as in Example 6. The results are reported in the following table.

field application. Untreated plants act as controls. Evaluation of the test is made 14 days after application of the

| | Compound | | | | | | | | | | | | | | | | | | | |
|---|---|---|---|---|---|---|---|---|---|---|---|---|---|---|---|---|---|---|---|---|
| | 1 | | | | | 2 | | | | | 14 | | | | 17 | | | 18 | | |
| | Rate of application in kg/hectare | | | | | | | | | | | | | | | | | | | |
| Plant | 2 | 1 | ½ | ¼ | ⅛ | 2 | 1 | ½ | ¼ | ⅛ | 2 | 1 | ½ | ¼ | 4 | 2 | 1 | ½ | 2 | 1 | ½ | ¼ |
| barley | 2 | 4 | 7 | 8 | 8 | 2 | 2 | 6 | 8 | 8 | 3 | 6 | 6 | 7 | — | — | — | — | — | — | — | — |
| wheat | 5 | 9 | 9 | 9 | 9 | 3 | 4 | 6 | 8 | 9 | 3 | 4 | 7 | 8 | 3 | 7 | 7 | 9 | 7 | 8 | 8 | 9 |
| rice | 6 | 7 | 7 | 9 | 9 | 2 | 6 | 7 | 7 | 8 | 6 | 7 | 7 | 9 | 6 | 7 | 7 | 9 | 9 | 9 | 9 | 9 |
| soybeans | 3 | 4 | 4 | 6 | 9 | 3 | 3 | 5 | 7 | 7 | 2 | 3 | 4 | 6 | 4 | 8 | 8 | 9 | 7 | 7 | 9 | 9 |
| avena fatua | 3 | 6 | 9 | 9 | 9 | 2 | 5 | 7 | 9 | 9 | 4 | 4 | 7 | 9 | 3 | 3 | 6 | 7 | 7 | 7 | 7 | 8 |
| alopecurus myos. | 2 | 2 | 3 | 9 | 9 | 1 | 2 | 6 | 7 | 9 | 3 | 3 | 4 | 4 | 3 | 3 | 4 | 4 | 7 | 9 | 9 | 9 |
| echinochloa crus galli | 1 | 1 | 2 | 4 | 4 | 1 | 1 | 2 | 4 | 4 | 2 | 2 | 4 | 6 | 8 | 9 | 9 | 9 | 2 | 2 | 3 | 4 |
| rottboellia exaltata | 4 | 5 | 7 | 8 | 8 | 2 | 3 | 4 | 7 | 8 | 4 | 4 | 6 | 7 | 4 | 5 | 6 | 9 | 7 | 8 | 9 | 9 |
| abutilon | 1 | 1 | 1 | 1 | 1 | 1 | 1 | 1 | 1 | 1 | 1 | 1 | 2 | 2 | 1 | 1 | 1 | 1 | 1 | 2 | 6 | 7 |
| xanthium | — | — | — | — | — | 1 | 1 | 1 | 1 | 1 | 2 | 2 | 3 | 5 | 2 | 3 | 3 | 3 | 1 | 3 | 3 | 4 |
| amaranthus retroflexus | 1 | 1 | 2 | 3 | 3 | 1 | 1 | 1 | 1 | 1 | 1 | 1 | 2 | 2 | — | — | — | — | — | — | — | — |
| chenopodium album | 1 | 1 | 1 | 6 | 6 | 1 | 1 | 1 | 1 | 1 | 1 | 1 | 1 | 1 | 1 | 2 | 3 | 4 | 1 | 3 | 5 | 5 |
| solanum nigrum | 1 | 1 | 1 | 2 | 6 | 1 | 1 | 1 | 2 | 2 | 1 | 1 | 1 | 1 | — | — | — | — | — | — | — | — |
| ipomoea purpurea | 1 | 1 | 1 | 2 | 2 | 1 | 1 | 1 | 1 | 1 | 1 | 1 | 1 | 1 | 1 | 2 | 2 | 3 | 2 | 2 | 2 | 3 |
| sinapis alba | 1 | 1 | 1 | 1 | 3 | 1 | 1 | 1 | 1 | 1 | 1 | 3 | 3 | 1 | 1 | 1 | 1 | 1 | 1 | 2 | 2 |
| chrysanthemum leucum | 1 | 1 | 1 | 1 | 1 | 1 | 1 | 1 | 1 | 1 | 1 | 1 | 2 | 3 | — | — | — | — | — | — | — | — |
| galium aparine | 1 | 1 | 1 | 1 | 1 | 1 | 1 | 1 | 2 | 2 | 3 | 1 | 1 | 2 | 2 | 2 | 3 | 7 | 3 | 3 | 3 | 4 |
| viola tricolor | 1 | 1 | 1 | 1 | 1 | 1 | 1 | 1 | 1 | 1 | 1 | 1 | 1 | 2 | 1 | 1 | 1 | 1 | 1 | 2 | 2 | 2 |
| veronica sp | 1 | 1 | 1 | 1 | 1 | 1 | 1 | 1 | 1 | 1 | 1 | 1 | 1 | 1 | — | — | — | — | — | — | — | — |

Even when applied at low rates of application the tested compounds of the formula I exhibit a pronounced action against the dicot weeds, and also against a number of monocots, without causing damage to the cultivated plants, e.g. wheat and rice.

EXAMPLE 8

Selective postemergence herbicidal action in rice

Rice plants which are 25 days old are transplanted into large rectangular asbestos cement containers in a greenhouse. Seeds of the weeds occurring in rice crops, *Echinochloa crus galli* and *Cyperus difformis*, are then sown between the rows of rice plants. The containers are well watered and kept at a temperature of about 25° C. and at high humidity. Twelve days later, when the weeds have emerged and reached the 2-3 leaf stage, the soil in each of the containers is covered with a layer of water to a height of 2.5 cm. The compound to be tested is then applied in the form of an emulsifiable concentrate with a pipette between the rows of plants. The emulsifiable concentrate is diluted and applied such that it corresponds to a field application rate of 4,2,1 and ½ kg/ha respectively. The test is evaluated 4 weeks later. The results are reported in the following table.

| | Compound | | | | | |
|---|---|---|---|---|---|---|
| | 1 | 2 | 14 | 17 | 18 | 21 |
| | Rate of application in kg/ha | | | | | |
| Plant | 4 2 1 ½ | 4 2 1 ½ | 4 2 1 ½ | 4 2 1 ½ | 4 2 1 ½ | 4 2 |
| rice | 5 6 6 7 | 3 3 4 5 | 5 6 7 8 | 5 5 6 6 | 7 8 9 9 | 6 7 |
| Echinochloa crus galli | 4 4 5 7 | 1 1 1 1 | 1 1 2 5 | 1 1 1 1 | 4 5 6 7 | 3 6 |
| cyperus difformis | 1 1 2 3 | 1 1 1 1 | 1 1 1 2 | 3 3 4 4 | 2 3 4 6 | 2 4 |

EXAMPLE 9

Desiccation and defoliation action in cotton

Cotton plants of the variety Deltapine are reared in earthenware pots in a greenhouse. After the first capsules have formed, the plants are sprayed with aqueous formulations of test compound at a rate of application corresponding to 1, 2, 0.6 and 0.3 kg/ha respectively in field application. Untreated plants act as controls. Evaluation of the test is made 14 days after application of the active ingredient by determining the degree of defoliation (percentage of fallen leaves) and of desiccation (drying out of the leaves remaining on the plant; 100%=all leaves desiccated or dropped).

The results are reported in the following table.

| Rate of application in kg/ha | Defoliation | | | Desiccation | | |
|---|---|---|---|---|---|---|
| | 0.3 | 0.6 | 1.2 | 0.3 | 0.6 | 1.2 |
| Compound 2 | 50% | 50% | 30% | 80% | 90% | 80% |
| 14 | 80% | 30% | 40% | 90% | 90% | 90% |

EXAMPLE 10

Growth inhibition of grasses

Seeds of *Lolium perenne, Poa pratensis, Festuca ovina, Dactylis glomerata,* Cynodon, barley and rye, are sown in plastic dishes filled with an earth/turf/sand mixture (6:3:1) and watered normally. The emergent grasses are cut back weekly to a height of 4 cm above the soil and treated 40 days after sowing and 1 day after the last cut with aqueous spray mixtures of compound 17. The rate of application corresponds to 0.5 and 2.5 kg of active ingredient per hectare. The growth of the grasses is compared that of an untreated control 21 days after application and the new growth is expressed as a percentage of the growth of untreated control grasses (=100%). The results are reported in the following table.

| | Plant | | | | | | |
|---|---|---|---|---|---|---|---|
| Rate of application in kg/ha | lolium | poa | festucca | dactylis | cynodon | barley | rye |
| 0.5 | 86% | 65% | 81% | 79% | — | 66% | 42% |
| 2.5 | 57% | 19% | 37% | 36% | 26% | 47% | 55% |

What is claimed is:
1. A compound of the formula

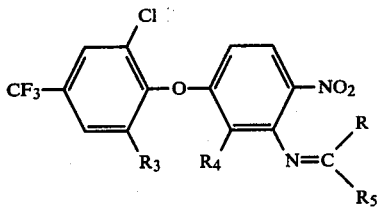

wherein

R is

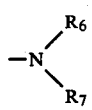

or $C_1$–$C_4$ alkoxy, one of $R_3$ and $R_4$ is hydrogen and the other is chlorine or hydrogen, $R_5$ is hydrogen or $C_1$–$C_4$ alkyl, $R_6$ is hydrogen, $C_1$–$C_4$ alkyl, $C_2$–$C_4$ alkenyl or $C_2$–$C_4$ alkynyl, and $R_7$ is hydrogen or $C_1$–$C_4$ alkyl, or $R_6$ and $R_7$ together with the nitrogen atom to which they are attached, can form a pyrrolidine, pyrroline, imidazolidine, pyrazolidine, piperidine, piperazine, morpholine, pyrazoline, imidazole, pyrrole or imidazoline ring.

2. A compound according to claim 1 in which R is

3. A compound according to claim 2 wherein $R_5$ is hydrogen.

4. N-[3-(2'-Chloro-4'-trifluormethylphenoxy]-6-nitrophenyl]-N',N'-dimethylformamidine according to claim 1.

5. N-[3-(2'-Chloro-4'-trifluormethylphenoxy)-6-nitrophenyl]-N',N'-dimethylacetamidine according to claim 1.

6. N-[2-Chloro-3-(2'-chloro-4'-trifluormethylphenoxy)-6-nitrophenyl]-N',N'-dimethylformamidine according to claim 1.

7. N-[3-(2',6'-Dichloro-4-trifluormethylphenoxy)-6-nitrophenyl]-N',N'-dimethylformamidine according to claim 1.

8. N-[3-(2',6'-Dichloro-4-trifluormethylphenoxy)-6-nitrophenyl]-N',N'-dimethylacetamidine according to claim 1.

9. N-[2-Chloro-3-(2'-chloro-4'-trifluormethylphenoxy)-6-nitrophenyl]-N',N'-dimethylacetamidine according to claim 1.

10. N-[3-(2'-Chloro-4'-trifluormethylphenoxy)-6-nitrophenyl]-ethoxyacetimide according to claim 1.

11. A herbicidal composition which comprises (1) a herbicidally effective amount of a compound according to claim 1 and (2) a carrier.

12. A method of selectively controlling weeds in crops of useful plants, which comprises applying to said crops a herbicidally effective amount of a compound according to claim 1.

13. A method of controlling weeds at a locus, which method comprises applying to said locus a herbicidally effective amount of a compound according to claim 1.

14. A method of controlling weeds postemergence in crops of cereals, rice and soybeans, which method comprises applying to said crops a herbicidally effective amount of a compound according to claim 1.

* * * * *